United States Patent
Fazzio et al.

(10) Patent No.: US 7,152,758 B2
(45) Date of Patent: Dec. 26, 2006

(54) SCENTED MATERIAL DISPENSE SYSTEM FOR A HAND-HELD DEVICE

(75) Inventors: Ronald Shane Fazzio, Loveland, CO (US); Richard Ruby, Menlo Park, CA (US); Kevin Patrick Killeen, Palo Alto, CA (US); Daniel B. Roitman, Menlo Park, CA (US); Jeremy Alfred Theil, Mountain View, CA (US)

(73) Assignee: Avago Technologies Wireless IP (Singapore) Pte. ltd., Singapore (SG)

( * ) Notice: Subject to any disclaimer, the term of this patent is extended or adjusted under 35 U.S.C. 154(b) by 86 days.

(21) Appl. No.: 10/919,669

(22) Filed: Aug. 17, 2004

(65) Prior Publication Data

US 2006/0037970 A1   Feb. 23, 2006

(51) Int. Cl.
*B67D 5/60*   (2006.01)
(52) U.S. Cl. .................. 222/145.1; 222/52; 222/94; 222/145.5; 222/145.6
(58) Field of Classification Search ............. 222/145.1, 222/145.5, 145.6, 52, 94, 136; 239/310
See application file for complete search history.

(56) References Cited

U.S. PATENT DOCUMENTS

| | | | |
|---|---|---|---|
| 4,570,824 A * | 2/1986 | Bolling ..................... 222/39 |
| 5,046,648 A * | 9/1991 | Herbstzuber ................ 222/638 |
| 5,223,182 A * | 6/1993 | Steiner et al. ................ 261/26 |
| 5,292,067 A * | 3/1994 | Jeffries et al. .................. 239/3 |
| 5,591,409 A * | 1/1997 | Watkins ..................... 422/110 |
| 5,969,353 A | 10/1999 | Hsieh |
| 6,267,297 B1 * | 7/2001 | Contadini et al. ............. 239/1 |
| 6,323,912 B1 | 11/2001 | McIntyre |
| 6,378,988 B1 | 4/2002 | Taylor et al. |
| 6,390,453 B1 | 5/2002 | Frederickson et al. |
| 6,554,203 B1 * | 4/2003 | Hess et al. .................... 239/69 |
| 6,619,559 B1 * | 9/2003 | Wohrle ........................ 239/34 |
| 6,712,287 B1 * | 3/2004 | Le Pesant et al. ............ 239/67 |
| 6,802,460 B1 * | 10/2004 | Hess et al. ................... 239/306 |
| 2002/0176802 A1 | 11/2002 | Chung et al. |
| 2003/0116195 A1 | 6/2003 | Weissgerber et al. |
| 2004/0003812 A1 * | 1/2004 | Manne ................... 128/204.11 |
| 2004/0235430 A1 * | 11/2004 | Ma et al. .................... 455/90.1 |
| 2005/0253289 A1 * | 11/2005 | Liou .......................... 261/142 |

* cited by examiner

*Primary Examiner*—Frederick C. Nicolas (57) ABSTRACT

A dispense system stores a scented material or materials and is provided with an electrical interface that is compatible with a hand-held device. The dispense system can be connected to the hand-held device and driven with the help of the hand-held device to dispense the scented material. The dispense system can be configured to store different scented materials that can be mixed to create different scents. Logic within the hand-held device supports the mixing and dispensing of the scented materials.

21 Claims, 7 Drawing Sheets

FIG.12

SCENTED MATERIAL DISPENSE SYSTEM FOR A HAND-HELD DEVICE

BACKGROUND OF THE INVENTION

There are many different types of electronic hand-held devices including mobile phones, personal digital assistants (PDAs), and music players (e.g., MP3 players). These hand-held devices appeal to a user's sense of sight through graphical user interfaces and to the user's sense of sound through speakers and microphones. Although sight and sound are effective in producing an acceptable user experience, the user experience provided by hand-held devices may be enhanced if the hand-held devices were able to appeal to other senses.

SUMMARY OF THE INVENTION

A dispense system stores a scented material or materials and is provided with an electrical interface that is compatible with a hand-held device. The dispense system can be connected to the hand-held device and is driven with the help of the hand-held device to dispense the scented material. The dispense system can be configured to store different scented materials that can be mixed to create different scents. Logic within the hand-held device supports the dispensing of the scented materials. For example, instructions for dispensing the scented materials can be programmed through the user interface of the hand-held device and executed by the processing system of the hand-held device. The dispense system is removable from a hand-held device and can be easily replaced to replenish the supply of scented materials or to change the available scents. In an embodiment, the dispense system has a standard interface that makes the dispense system compatible with a wide range of hand-held devices.

BRIEF DESCRIPTION OF THE DRAWINGS

Throughout the description similar reference numbers are used to identify similar elements.

DETAILED DESCRIPTION

A dispense system stores a scented material or materials and is provided with an electrical interface that is compatible with a hand-held device. The dispense system can be connected to the hand-held device and driven with the help of the hand-held device to dispense the scented material. The dispense system can be configured to store different scented materials that can be mixed to create different scents. Logic within the hand-held device supports the dispensing of the scented materials.

Figure 1:
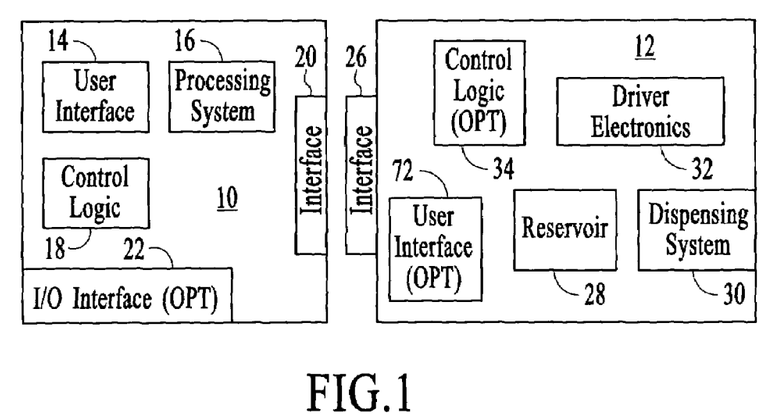
FIG. 1 depicts a hand-held device and a removable dispense system that are used in conjunction with each other to dispense scented materials in accordance with an embodiment of the invention.

FIG. 1 depicts a hand-held device 10 and a removable dispense system 12 that are used in conjunction with each other to dispense scented materials. The hand-held device is any hand-held device that is capable of supporting the dispensing of scented materials from the removable dispense system. Examples of hand-held devices that may be used in conjunction with the removable dispense system include mobile phones, PDAs, music players, and other types of hand-held devices.

The hand-held device 10 includes a user interface 14, a processing system 16, control logic 18, and an interface 20. The hand-held device may also include an optional input/output (I/O) interface 22. The user interface allows a user to control the hand-held device and may include any type of user interface, for example, a display screen, a keypad, a touch screen, a pen-based system, a voice activated system, or any combination thereof. As is described in more detail below, the user interface is also used to control the removable dispense system 12. User interfaces for hand-held devices are well-known and the type of user interface is not critical to the invention.

The processing system 16 of the hand-held device 10 performs the processing to support operation of the hand-held device. The processing system may include hardware, software, firmware or any combination thereof. For example, in a mobile phone or a PDA, the processing system may include memory and a processor for storing and executing software code. The processor may be a general function processor, an application specific integrated circuit (ASIC), or any combination thereof. Alternatively, the processor may be as simple as an analog circuit.

The control logic 18 of the hand-held device 10 supports operation of the removable dispense system 12. The control logic may include hardware, software, firmware or any combination thereof. The control logic may be embodied as software code that is executed by the processing system 16. Although the control logic is shown as a separate functional element from the processing system for description purposes, the control logic may be integrated within the processing system of the hand-held device.

The interface 20 of the hand-held device 10 allows the hand-held device to communicate with the removable dispense system 12. The interface may be an electrical interface in the form of a plug or a jack. The interface may conform to an interface standard that allows different types of removable devices to communicate with the hand-held device. In an embodiment, the interface is an internationally recognized standard interface, such as Universal Serial Bus (USB), MultiMediaCard (MMC), reduced size (RS)—MMC, Personal Computer Memory Card International Association (PCMCIA), Compact Flash, Memory Stick, Secure Digital, Firewire, Peripheral Computer Interconnect (PCI), Integrated Device Electronics (IDE), Advanced Technology Attachment (ATA), or serial ATA.

The hand-held device 10 may also include an I/O interface 22 for communications with other devices or systems. For example, the I/O interface may be a wireless interface such as those used in mobile phones and PDAs. Wireless interfaces are well-known in the field of hand-held devices. The I/O interface may also include any other type of I/O interface such as infrared or wireline interfaces.

Referring now to the removable dispense system 12 depicted in FIG. 1, the removable dispense system includes an interface 26, a reservoir 28, a dispensing system 30, driver electronics 32, optional control logic 34 and an optional user interface 72. The interface is compatible with the interface 20 of the hand-held device 10. The interface allows communications between the hand-held device and the removable dispense system. In particular, when connected to the interface of the hand-held device, the interface of the removable dispense system allows control signals to be communicated between the hand-held device and the removable dispense system. In an embodiment, the interface is a standard interface such as USB, MMC, RS-MMC, PCMCIA, Compact Flash, Memory Stick, Secure Digital, Firewire, PCI, IDE, ATA, or serial ATA. Providing the removable dispense system with a standard interface allows the removable dispense system to be compatible with any hand-held device that uses the same standard interface and will enable the removable dispense system to be easily adopted by users of hand-held devices.

The reservoir 28 of the removable dispense system 12 stores a scented material. Specifics of the reservoir depend on the type of scented material that is stored and the mechanism that is used to dispense the scented material. The scented material stored in the reservoir may be a fluid or a solid at standard temperature and pressure conditions. In an embodiment, the reservoir is a chamber that is formed in a substrate material, although this is not critical. The reservoir may be configured for a single use or it may be refillable. The reservoir may be removable from the removable dispense system for replacement or refilling.

The dispensing system 30 functions to dispense the scented material from the removable dispense system 12. The dispensing system includes a mechanism to move the scented material from the reservoir 28 and to dispense the scented material from the removable dispense system. The mechanism used to move the scented material from the reservoir and out of the removable dispense system depends on the type of scented material that is stored in the reservoir. The dispense system may utilize, for example, piezoelectric, thermal, chemical release, photo release, electrochemical, mechanical, or pneumatic mechanisms or any combination thereof depending on the scented material involved. The dispensing system may dispense the scented material as, for example, a spray, a drop, a liquid stream, a vapor, aerosol, or a gas.

In an embodiment, the scented material is stored in a solid form. For example, the scented material is stored as a wax-like material that is formed of scented material molecules that are held together by a binding agent. Techniques for dispensing a scented material that is stored in a solid form may include heating the solid material to transform the solid material into a vapor that can be transported through the system and dispensed from the system. The dispensing system may include a combination of a channel, a nozzle, and the supporting mechanism(s) required to move the vaporized scented material through the channel and out the nozzle. Examples of systems for dispensing scented materials that are stored in a solid form are described below with reference to FIG. 6–9.

In another embodiment, the scented material is stored as a fluid. The fluid can be dispensed using, for example, microfluidic techniques. Microfluidic techniques for dispensing a scented fluid may include, for example, piezoelectric, thermal, chemical release, photo release, electrochemical, mechanical, or pneumatic mechanisms, or any combination thereof. The dispensing system may include a combination of a channel, a nozzle, and the supporting microfluidic mechanism(s) required to move the scented fluid through the channel and out the nozzle.

In still another embodiment, the scented material is stored in a microencapsulated form. The microencapsulated scented material may be, for example, released from its microencapsulation upon dispensing or dispensed from the removable dispense system in a microencapsulated form and subsequently released, for example, by physical contact such as rubbing.

The driver electronics 32 of the removable dispense system 12 are any electronics that are necessary to dispense the scented materials. Exemplary driver electronics are dependent on the dispense technique that is used and may be as simple as a potential difference (i.e., a voltage drop) or as complicated as an analog, digital, or mixed signal device that generates a signal waveform as either a current or voltage.

Control logic 34 may be incorporated within the removable dispense system 12 to process control signals that are received from the hand-held device 10. The control logic may include specialized functionality that is difficult or impractical to incorporate into the hand-held device. An example of the control logic includes preprogrammed dispensing functionality such as preprogrammed dispensing characteristics (e.g., liquid stream, spray, timed dispensing, etc.).

In an embodiment, the removable dispense system 12 has its own user interface 72, which allows a user to control the removable dispense system. The user interface may be as simple as one or more buttons. Alternatively, the user interface may include a display screen, a keypad, a touch screen, a pen-based system, a voice activated system, or any combination thereof.

In an exemplary operation, control signals are generated by the control logic 18 of the hand-held device 10. The control signals may be generated as a result of, for example, user inputs through the user interface 14, information received from the I/O interface 22, or any combination thereof. The control signals may dictate the timing of scented material dispensing, the magnitude of the scented material dispensing, the type of dispensing (e.g., liquid stream, fine/coarse spray, drop, vapor, aerosol, or gas) or any other characteristic of the material dispensing. The control signals are communicated to the removable dispense system 12 through the interfaces 20 and 26 of the hand-held device and the removable dispense system. Once received at the removable dispense system, the control signals are provided to the driver electronics 32 and in response, the driver electronics drive the particular mechanism of the dispensing system 30 to dispense the scented material.

The reservoir 28, dispensing system 30, and driver electronics 32 can be implemented in many different configurations. Additionally, although the reservoir, dispensing system, and driver electronics are shown as distinct elements, they may be partially integrated as depicted in FIG. 2, or fully integrated, depending on the type of scented material and the dispense mechanism used.

Figure 2:
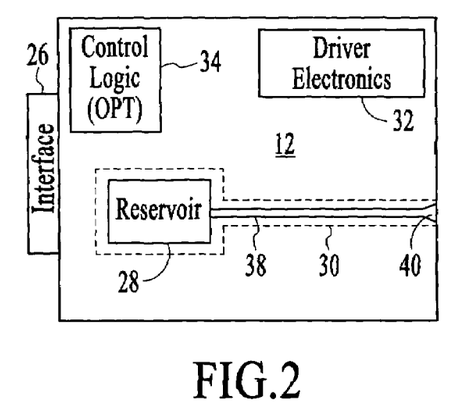
FIG. 2 depicts an embodiment of the removable dispense system from FIG. 1 in which the dispensing system includes a channel and a nozzle.

FIG. 2 depicts an embodiment of the removable dispense system 12 from FIG. 1. In the embodiment of FIG. 2, the dispensing system of the removable dispense system includes a channel 38 and a nozzle 40 that are in material communication with the reservoir. Scented material from the reservoir is forced into and through the channel using a dispense technique (e.g., thermal, mechanical, etc.). The scented material may be dispensed from the removable dispense system through the nozzle using, for example, piezoelectric, thermal, chemical release, photo release, electrochemical, mechanical, or pneumatic mechanisms, or any combination thereof. For example, a thermal-based dispense technique may include heating elements integrated around the reservoir and the channel.

Figure 3:
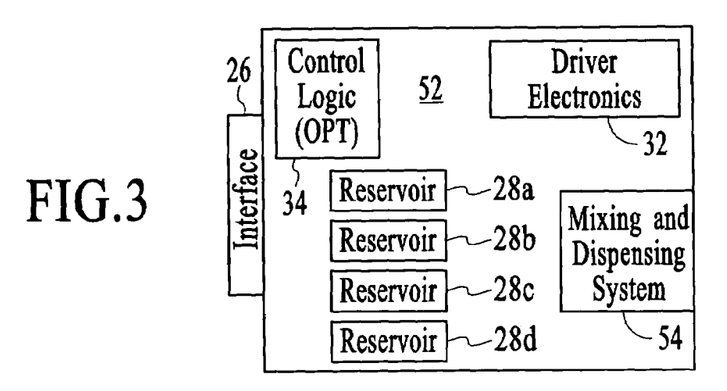
FIG. 3 depicts an embodiment of a removable dispense system that is similar to the removable dispense system of FIG. 1 except that it includes four reservoir portions and a mixing and dispensing system.

In an embodiment, the removable dispense system is able to store and mix different scented materials to create a wider variety of scents. FIG. 3 depicts an embodiment of a removable dispense system 52 that is similar to the removable dispense system 12 of FIG. 1 except that reservoir 28 includes four reservoir portions 28a, 28b, 28c, and 28d and the removable dispense system 52 additionally includes a mixing and dispensing system 54. The four reservoir portions can be filled with scented materials having different scents, which can be mixed by the mixing and dispensing system to create a variety of different scents. Although the removable dispense system depicted in FIG. 3 has four different reservoir portions, it is possible to have more or less than four reservoir portions.

In an exemplary operation, control signals are generated by the control logic 18 of the hand-held device 10 as a result of, for example, user inputs through the user interface 14, information received through the I/O interface 20, or any combination thereof. In addition to the dispense characteristics described above with reference to FIG. 1, the control signals may dictate how to dispense the different scented materials. Instructions on the types and amounts of scented materials to dispense to create a particular scent are referred to herein as a "recipe" of a scent.

Recipes are fully programmable and can be, for example, created at the hand-held device, received at the hand-held device through the I/O interface, or preprogrammed into the hand-held device or the removable dispense system 52. In an embodiment, the removable dispense system and the hand-held device can be preprogrammed with different recipes to create different scents. The different recipes can be accessed and initiated through the user interface of the hand-held device or through the optional user interface 72 (FIG. 1) of the removable dispensing system.

Control signals that are generated at the hand-held device 10 are communicated to the removable dispense system 52 through the interfaces 20 and 26 of the hand-held device and the removable dispense system. The control signals are provided to the driver electronics 32 and in response, the driver electronics drive the mechanism(s) that dispense the scented materials. The control signals may control, for example, the magnitude and duration of a temperature increase in a thermally activated dispense system, an applied electrical field in an electrophoresis-based dispense system, or the pump speed and duration in a micropump-based dispense system. The scented materials can be dispensed as, for example, a spray (e.g., an atomized spray), a drop, a liquid stream, a vapor, aerosol, or a gas.

Figure 4:
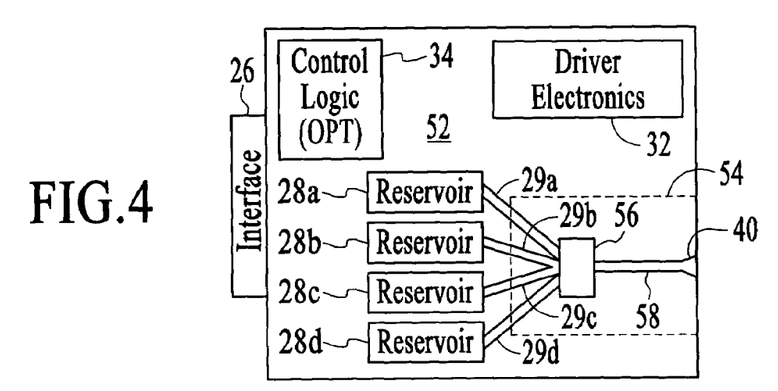
FIG. 4 depicts an embodiment of the removable dispense system from FIG. 3 in which the mixing and dispensing system includes a mixing chamber.

The reservoir portions 28a–28d and the mixing and dispensing system 54 can be implemented in many different configurations. FIG. 4 depicts an embodiment of the removable dispense system 52 from FIG. 3 in which the mixing and dispensing system includes a mixing chamber 56, channels 29a, 29b, 29c, and 29d between the reservoir portions 28a–28d and the mixing chamber, a nozzle 40, and a channel 58 between the mixing chamber and the nozzle. The reservoir portions, channels, mixing chamber, and nozzle are in material communication with one another and enable the scented materials in the four reservoir portions to be mixed and dispensed from the removable dispense system. In an embodiment, the mixing chamber may be implemented as, for example, intersecting fluid channels, a passive chamber, a chamber with active components such as a mixing actuator, or a region that produces mixing through chemical reactions, electrostatic potentials, magnetic fields, or electrodynamic effects. Other mixing mechanisms are also possible.

Although in the embodiment of FIG. 4 the mixing and dispensing system 54 includes a mixing chamber 56, in an alternative embodiment, the mixing of the scented materials is performed in a common channel. For example, the four channels from the reservoir portions come together to a single channel in which mixing occurs.

Figure 5:
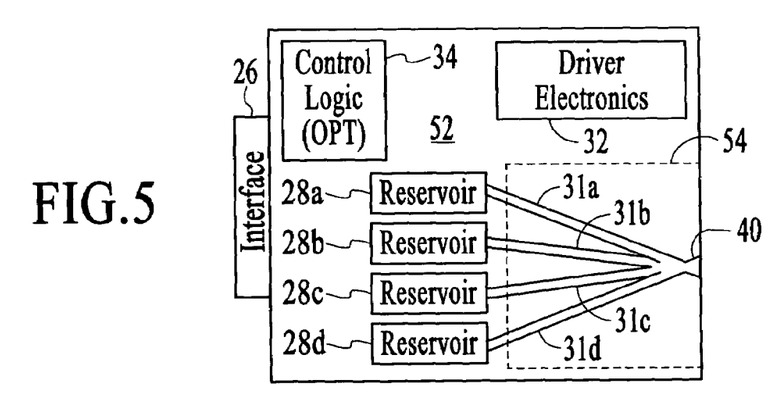
FIG. 5 depicts an embodiment of the mixing and dispensing system of FIG. 3 in which the scented materials are mixed as they are dispensed from the removable dispense system.

In another alternative embodiment, the mixing of the scented materials occurs upon dispense. FIG. 5 depicts an embodiment of the mixing and dispensing system 54 of FIG. 3 in which the scented materials are mixed as they are dispensed from the removable dispense system. In the embodiment of FIG. 5, the scented materials are mixed as they are dispensed from a common nozzle 40 via channels 31a, 31b, 31c, and 31d. Alternatives to this approach may include, for example, the channels having dedicated nozzles that are close in proximity to each other such that the scented materials are mixed after they are dispensed.

Figure 6:
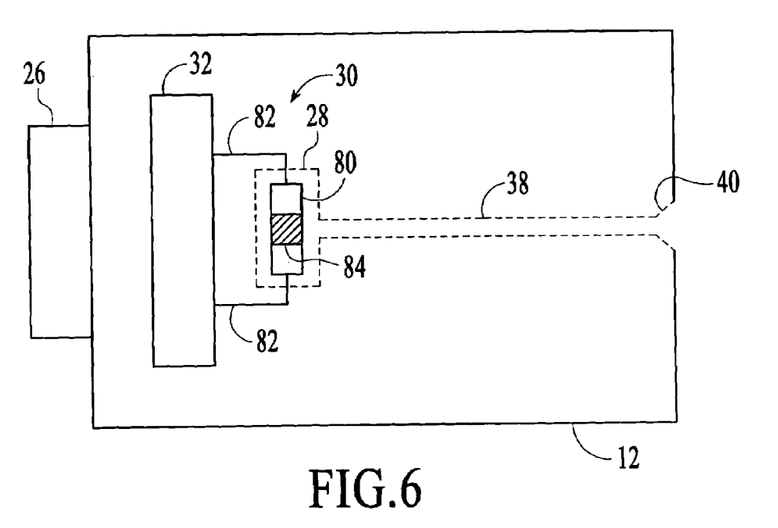
FIG. 6 depicts an embodiment of a removable dispense system that is configured to dispense scented material that is stored in a solid form.

As described above, the removable dispense system may be configured to dispense scented material that is stored in a solid form. FIG. 6 depicts an embodiment of a removable dispense system that is configured to dispense scented material that is stored in a solid form. The system includes an interface 26, driver electronics 32, a reservoir 28, and a dispensing system 30. In the embodiment of FIG. 6, the dispensing system includes a heating element 80, electrical connections 82, a channel 38, and a nozzle 40. The scented material 84 is located on, or in close proximity to, the heating element. The heating element, electrical connectors, and drive electronics are located on a substrate, which is covered by a lid (not shown). The lid has features that create the reservoir and the channel when the lid is secured to the substrate.

Figure 7:
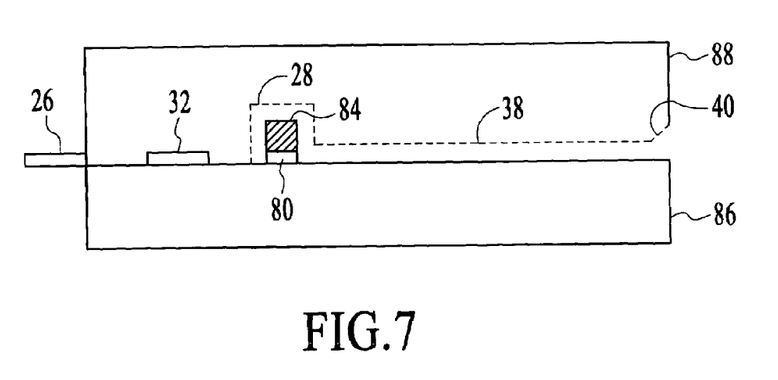
FIG. 7 is a side view of the removable dispense system of FIG. 6.

FIG. 7 is a side view of the removable dispense system of FIG. 6, which shows the heating element 80 and the solid-form scented material 84 on a substrate 86 and a lid 88. The lid includes features that form the reservoir 28 and the channel 38 when the lid is secured to the substrate.

In an exemplary operation, control signals are generated by the hand-held device (not shown) and communicated through the interfaces 20 and 26 of the hand-held device and the removable dispense system 12. The control signals cause the heating element 80 to apply heat to the solid form scented material 84. The applied heat causes a portion of the scented material to vaporize and the vapor flows through the channel 38. The vapor is ultimately dispensed from the system through the nozzle 40. The characteristics of the dispensing are a function of how the heating element is driven (e.g., the magnitude and timing).

Figure 8:
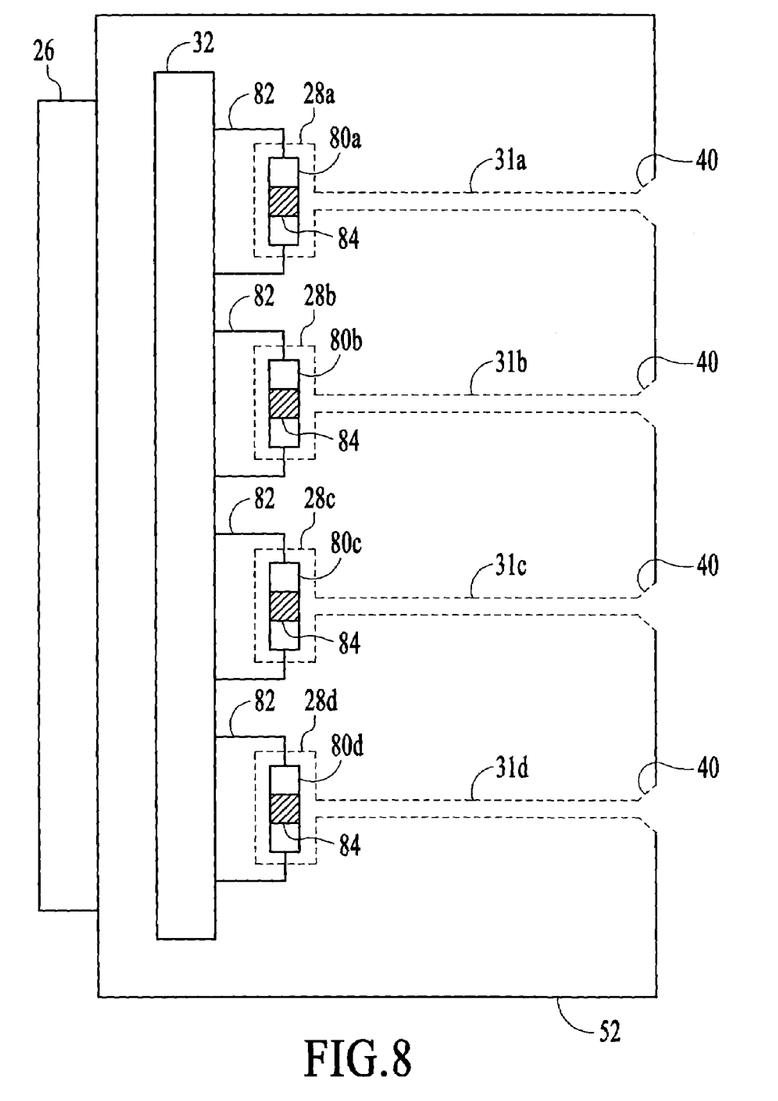
FIG. 8 depicts an embodiment of a removable dispense system that is similar to the system of FIGS. 6 and 7 except that it includes multiple scented materials and the systems to store and dispense the materials.

A removable dispense system that utilizes a scented material that is stored in a solid form can also be configured to store multiple materials with different scents. FIG. 8 depicts an embodiment of a removable dispense system 52 that is similar to the system of FIGS. 6 and 7 except that it includes multiple scented materials 84 that are in a solid form and the systems to store and dispense the materials. In particular, the system includes an interface 26, driver electronics 32, reservoir portions 28a–28d, heating elements 80a–80d, channels 31a–31d, and nozzles 40. In the embodiment of FIG. 8, the scented materials are mixed after they are dispensed from the removable dispense system.

Figure 9:
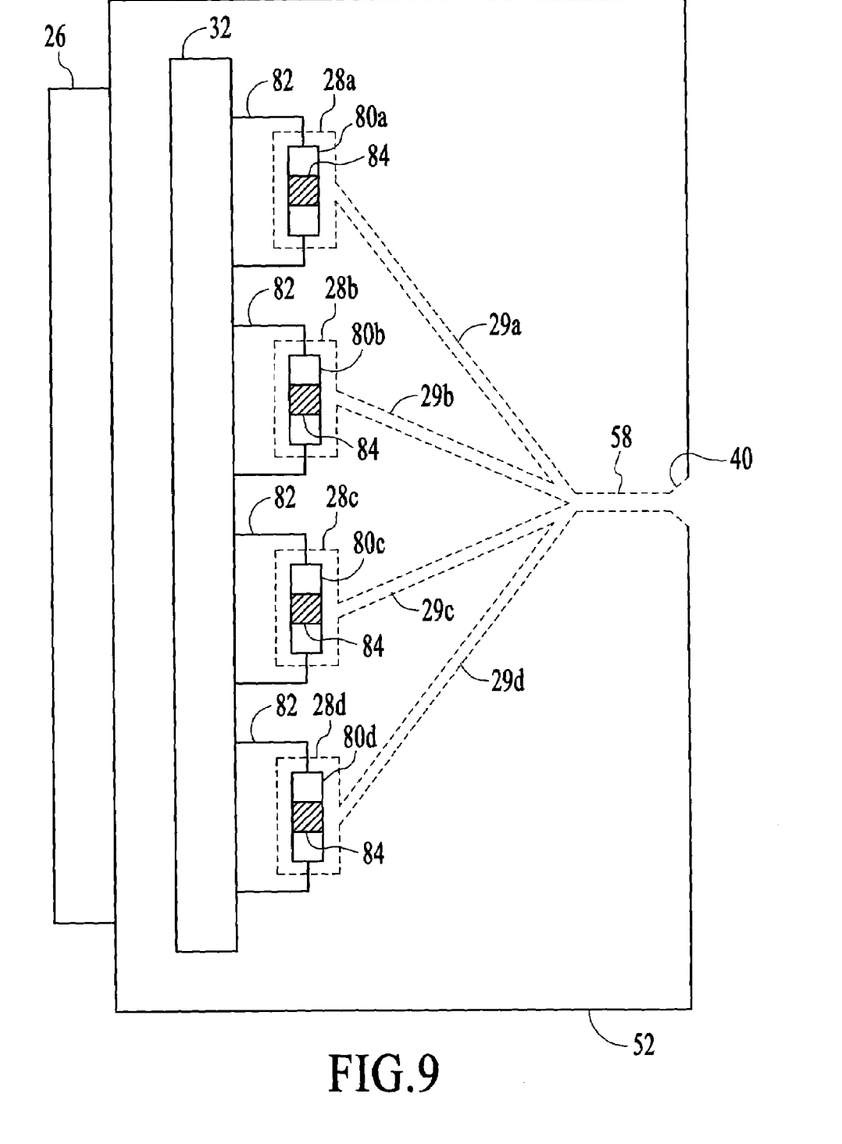
FIG. 9 depicts an embodiment of a removable dispense system that is similar to the system of FIG. 8 except that vaporized scented materials are mixed within the removable dispense system before being dispensed.

FIG. 9 depicts an embodiment of a removable dispense system 52 that is similar to the system of FIG. 8 except that the vaporized scented materials are mixed within the removable dispense system before being dispensed. In the system of FIG. 9, the four channels 29a–29d that run from the four different reservoir portions 28a–28d are combined into a common channel 58. The scented material is mixed within the common channel before being dispensed.

Because the removable dispense systems 12 and 52 interface with a hand-held device 10, the complexity of the removable dispense system can be kept to a minimum. That is, the removable dispense system is only required to include the interface 26, the driver electronics 32, the reservoir(s) 28, the dispensing system 30, or the mixing and dispensing system 54. This makes the removable dispense system cheaper to produce. Additionally, because hand-held devices are able to support more and more functionality, they are often equipped with processing capability that is flexible and programmable. This allows the hand-held device to be easily configured to support the removable dispense system.

Figure 10:
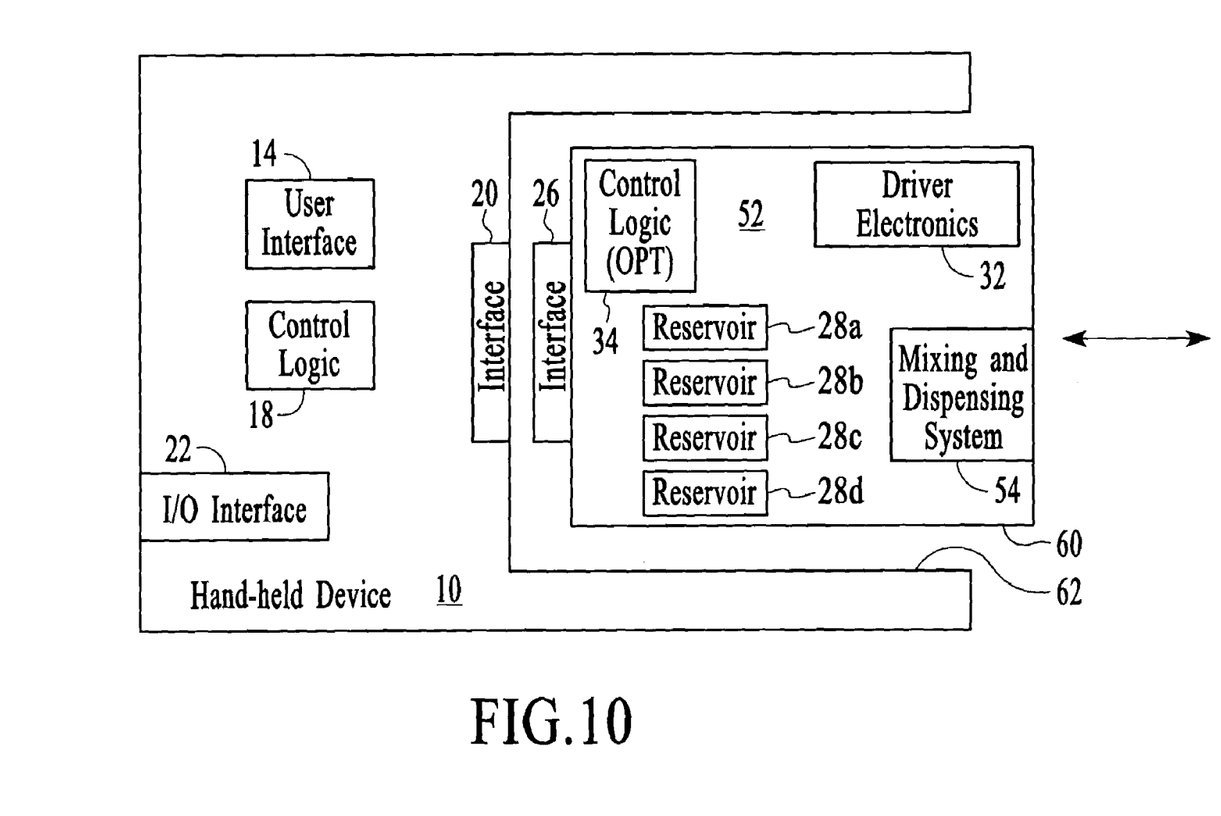
FIG. 10 depicts an embodiment of a hand-held device and a removable dispense system in which the structural shell of the removable dispense system is compatible with a structural interface of the hand-held device.

In some cases, the interfaces of the hand-held device and the removable dispense system include enough structural support to securely attach the removable dispense system to the hand-held device. For example, if the removable dispense system is small and light, a plug-type interface may provide sufficient structural support between the hand-held device and the removable dispense system. In other embodiments, the hand-held device and the removable dispense system may include compatible structural interfaces in addition to the electrical interfaces that enable the two devices to be structurally connected together. For example, the removable dispense system may be packaged in a structural shell that snaps into a compatible structural interface of the hand-held device. FIG. 10 depicts an embodiment of a hand-held device 10 and a removable dispense system 52 in which the structural shell 60 of the removable dispense system is compatible with a structural interface 62 of the hand-held device. In an embodiment, the structural interface of the hand-held device and the shell of the removable dispense system include attachment features (not shown), which allow the removable dispense system to be securely locked into the hand-held device.

Figure 11:
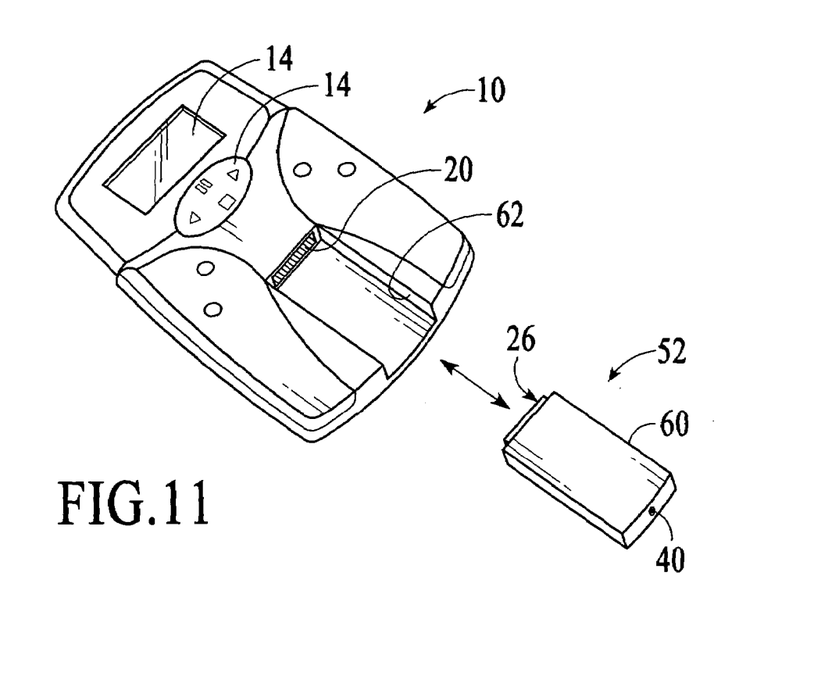
FIG. 11 depicts a perspective view of a hand-held device that includes a structural interface that is compatible with a removable dispense system.

In an embodiment, the structural interface 62 of the hand-held device is designed to support other devices that support the operation of the hand-held device. For example, the structural interface of the hand-held device may be designed to store a memory device that is used to store files such as digitally recorded music. In this case, the shell 60 of the removable dispense system is designed to be compatible with the existing structural interface of the hand-held device. FIG. 11 depicts a perspective view of a removable dispense system 52 with a structural shell 60 that is compatible with a structural interface 62 of a hand-held device 10.

Figure 12:
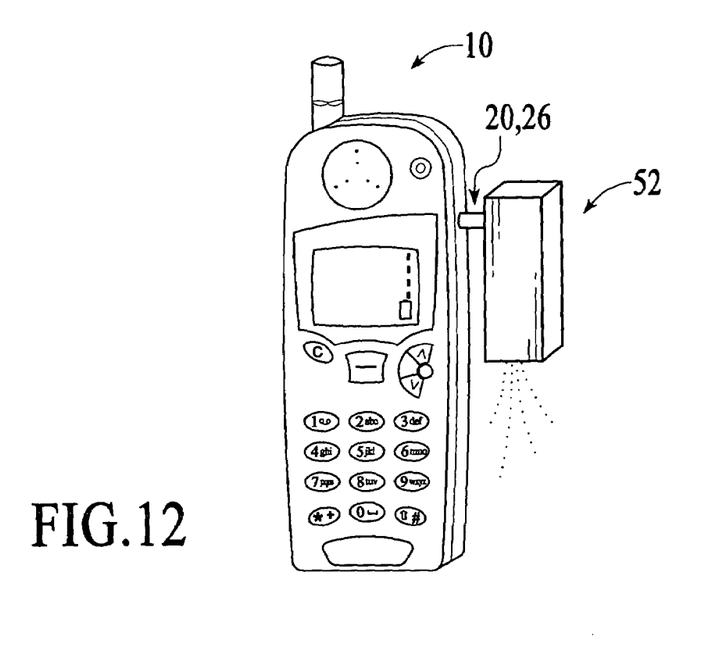
FIG. 12 depicts a hand-held device and a removable dispense system that are connected by an interface such as a plug-type interface.

In other embodiments, the hand-held device 10 and the removable dispense system 52 do not have a compatible structural interface and shell as described with reference to FIG. 11. FIG. 12 depicts a perspective view of a hand-held device 10 and a removable dispense system 52 that are connected by an interface that includes less structural support than the example of FIG. 11. In the example of FIG. 12, the interfaces 20 and 26 between the hand-held device and the removable dispense system consists of the male and female portions of a plug-type interface.

In the embodiments of FIGS. 1–12, the interfaces of the hand-held device and the removable dispense system are physically connected to each other during operation. However, it is possible that the interface does not involve a physical connection. For example, the interface between the hand-held device and the removable dispense system may involve a wireless radio frequency (e.g., Bluetooth and WiFi) or infrared connection.

In an embodiment, the removable dispense system is a "disposable" device that is used until the scented materials are gone and then discarded. In another embodiment, the reservoir(s) of the removable dispense system is/are refillable such that the removable dispense system can be reused.

The power consumed by the removable dispense system can be provided from the hand-held device through the respective interfaces. Alternatively, the removable dispense system may be provided with its own power supply.

Although the reservoir(s), driver electronics, dispensing and mixing systems are depicted in certain configurations in the examples described above, the elements may be integrated in other configurations.

Although specific embodiments in accordance with the invention have been described and illustrated, the invention is not limited to the specific forms and arrangements of parts so described and illustrated. The invention is limited only by the claims.

What is claimed is:

1. A system for dispensing scented material, the system comprising:
    a reservoir for storing scented material;
    a dispensing system configured to dispense the scented material stored in the reservoir;
    driver electronics operatively associated with the dispensing system configured to control the dispensing of the scented material; and
    an interface configured to interface wit a hand-held device, the interface being in electrical signal communication with the driver electronics;
    wherein the reservoir comprises reservoir portions, each for storing a different scented material and wherein the system additionally comprises a mixing system for mixing scented materials that are stored in the reservoir portions.

2. The system of claim 1 wherein the mixing system is responsive to control signals received from the hand-held device.

3. The system of claim 1 wherein the interface is compatible with a standard interface of the hand-held device.

4. The system of claim 1 wherein the reservoir, the dispensing system, the driver electronics, and the interface are incorporated into a structural shell compatible with a structural interface of the hand-held device.

5. The system of claim 1 wherein the driver electronics are responsive to control logic of the hand-held device.

6. The system of claim 1 wherein the scented material is stored as a solid and wherein the dispensing system includes a thermal dispense system.

7. The system of claim 1 wherein the scented material is stored as a fluid and wherein the dispensing system includes a microfluidic system.

8. The system of claim 1 wherein the scented material is stored in a microencapsulated form.

9. The system of claim 1 further comprising a user interface configured to allow control of the driver electronics.

10. A system for dispensing scented materials, the system comprising:
    reservoir portions for storing scented materials;
    a mixing and dispensing system configured to mix the scented materials from the reservoir portions and dispense the scented materials that are stored in the reservoir portions;
    driver electronics operatively associated with the mixing and dispensing system configured to control the mixing and dispensing of the scented materials; and
    an interface configured to interface with a hand-held device, the interface being in electrical signal communication with the driver electronics.

11. The system of claim 10 wherein the interface is compatible with a standard interface of the hand-held device.

12. The system of claim 10 wherein the reservoir portions, the mixing and dispensing system, the driver electronics, and the interface are incorporated into a structural shell compatible with a structural interface of the hand-held device.

13. The system of claim 10 wherein the driver electronics are responsive to control logic of the hand-held device.

14. The system of claim 10 wherein the scented materials are stored as solids and wherein the dispensing system includes a thermal dispense system.

15. The system of claim 10 wherein the scented materials are stored as fluids and wherein the dispensing system includes a microfluidic system.

16. A hand-held device comprising:
    a removable dispense system comprising:
        a reservoir for storing scented material;
        a dispensing system configured to dispense the scented material stored in the reservoir;
        driver electronics operatively associated with the dispensing system configured to control the dispensing of the scented materials; and
        a first interface in electrical signal communication with the driver electronics; and
    a second interface that is compatible with the first interface;
    wherein the reservoir comprises reservoir portions, each for storing a different scented material and wherein the hand-held device additionally comprises a mixing system for mixing the scented materials that are stored in the reservoir portions.

17. The hand-held device of claim 16 wherein the driver electronics is responsive to control signals from the hand-held device.

18. The hand-held device of claim 16 further comprising control logic configured to provide electrical control signals to the driver electronics of the removable dispense system through the first and second interfaces and a user interface configured to allow control of the control logic.

19. The hand-held device of claim 16 further comprising an input/output interface for receiving recipes for mixing the scented materials stored in the reservoir portions.

20. A system for dispensing scented material, the system comprising:
    a reservoir for storing scented material;
    a dispensing system configured to dispense the scented material stored in the reservoir;
    driver electronics operatively associated with the dispensing system configured to control the dispensing of the scented material; and
    an interface configured to interface with a hand-held device, the interface being in electrical signal communication with the driver electronics;
    wherein the scented material is stored as a solid and wherein the dispensing system includes a thermal dispense system.

21. A hand-held device comprising:
    a removable dispense system comprising:
        a reservoir for storing scented material;
        a dispensing system configured to dispense the scented material stored in the reservoir;
        driver electronics operatively associated with the dispensing system configured to control the dispensing of the scented materials; and
        a first interface in electrical signal communication with the driver electronics;
    a second interface that is compatible with the first interface; and
    control logic configured to provide electrical control signals to the driver electronics of the removable dispense system through the first and second interfaces and a user interface configured to allow control of the control logic.

* * * * *

UNITED STATES PATENT AND TRADEMARK OFFICE
CERTIFICATE OF CORRECTION

PATENT NO. : 7,152,758 B2  Page 1 of 1
APPLICATION NO. : 10/919669
DATED : December 26, 2006
INVENTOR(S) : Ronald Shane Fazzio et al.

It is certified that error appears in the above-identified patent and that said Letters Patent is hereby corrected as shown below:

Title Page, Column 1, (Assignee), Line 2, delete "ltd.," and insert -- Ltd., --;

Column 8, Line 55, Claim 1, delete "wit" and insert -- with --.

Signed and Sealed this

First Day of June, 2010

David J. Kappos
*Director of the United States Patent and Trademark Office*